(12) United States Patent
Glocker et al.

(10) Patent No.: US 8,894,824 B2
(45) Date of Patent: Nov. 25, 2014

(54) POROUS COATINGS FOR BIOMEDICAL IMPLANTS

(75) Inventors: David A. Glocker, West Henrietta, NY (US); Mark M. Romach, Spencerport, NY (US)

(73) Assignee: Isoflux, Inc., Rochester, NY (US)

( * ) Notice: Subject to any disclaimer, the term of this patent is extended or adjusted under 35 U.S.C. 154(b) by 1409 days.

(21) Appl. No.: 11/168,050

(22) Filed: Jun. 28, 2005

(65) Prior Publication Data

US 2006/0004466 A1    Jan. 5, 2006

Related U.S. Application Data

(60) Provisional application No. 60/583,416, filed on Jun. 28, 2004.

(51) Int. Cl.
| | |
|---|---|
| *C23C 14/00* | (2006.01) |
| *C23C 14/32* | (2006.01) |
| *C23C 14/22* | (2006.01) |
| *A61L 27/30* | (2006.01) |
| *A61F 2/30* | (2006.01) |

(52) U.S. Cl.
CPC ............. *C23C 14/225* (2013.01); *A61L 27/306* (2013.01); *A61F 2310/00485* (2013.01); *A61F 2002/3098* (2013.01); *A61F 2310/00544* (2013.01); *A61F 2310/0088* (2013.01); *A61F 2310/00449* (2013.01); *A61F 2310/00497* (2013.01); *A61F 2/30767* (2013.01); *A61F 2310/00407* (2013.01); *A61F 2002/30929* (2013.01); *A61F 2310/0097* (2013.01)
USPC .................................. 204/192.1; 204/192.15

(58) Field of Classification Search
USPC ............... 435/6; 623/1.34; 204/192.1, 192.15
See application file for complete search history.

(56) References Cited

U.S. PATENT DOCUMENTS

| | | |
|---|---|---|
| 3,884,793 A | 5/1975 | Penfold et al. |
| 3,919,678 A | 11/1975 | Penfold et al. |
| 3,995,187 A | 11/1976 | Penfold et al. |
| 4,030,986 A | 6/1977 | Shinskey |
| 4,031,424 A | 6/1977 | Penfold et al. |

(Continued)

FOREIGN PATENT DOCUMENTS

| | | |
|---|---|---|
| WO | WO 97/16137 | 5/1997 |
| WO | WO 97/26026 | 7/1997 |

(Continued)

OTHER PUBLICATIONS

Sit, J. C., et al. "Thin film microstructure control using glancing angle deposition by sputtering." J. Mater. Res 14.4 (Apr. 1999).*

(Continued)

*Primary Examiner* — Rodney McDonald
*Assistant Examiner* — Ibrahime A Abraham
(74) *Attorney, Agent, or Firm* — Simpson & Simpson, PLLC

(57) ABSTRACT

A medical implant has a microscopically rough outer coating that serves to bond the implant to animal tissue. The coating is applied to the implant by physical vapor deposition. The coating preferable is applied via a generally oblique coating flux or a low energy coating flux. In some embodiments, the coating has pores. The pores can contain a drug, which can diffuse over a period of time. The coating may be partially nonporous to protect the implant from corrosion. The coating can have an outer porous layer that can bond with animal tissue easily.

23 Claims, 7 Drawing Sheets

(56) References Cited

U.S. PATENT DOCUMENTS

| | | | |
|---|---|---|---|
| 4,041,353 A | 8/1977 | Penfold et al. | |
| 4,111,782 A | 9/1978 | Penfold et al. | |
| 4,116,793 A | 9/1978 | Penfold et al. | |
| 4,116,794 A | 9/1978 | Penfold et al. | |
| 4,132,612 A | 1/1979 | Penfold et al. | |
| 4,132,613 A | 1/1979 | Penfold et al. | |
| 4,440,178 A | 4/1984 | Bussard et al. | |
| 4,603,704 A * | 8/1986 | Mund et al. | 607/116 |
| 4,611,604 A | 9/1986 | Botvidsson et al. | |
| 4,784,161 A | 11/1988 | Skalsky et al. | |
| 4,844,099 A | 7/1989 | Skalsky et al. | |
| 4,915,805 A * | 4/1990 | Rust | 204/192.12 |
| 4,934,881 A | 6/1990 | Tsujimura et al. | |
| 5,282,844 A | 2/1994 | Stokes et al. | |
| 5,282,861 A | 2/1994 | Kaplan | |
| 5,607,442 A | 3/1997 | Fischell et al. | |
| 5,607,463 A | 3/1997 | Schwartz et al. | |
| 5,669,909 A | 9/1997 | Zdeblick et al. | |
| 5,807,407 A | 9/1998 | England et al. | |
| 5,824,045 A | 10/1998 | Alt | |
| 5,984,967 A | 11/1999 | Zdeblick et al. | |
| 5,991,667 A | 11/1999 | Feith | |
| 6,063,442 A | 5/2000 | Cohen et al. | |
| 6,099,561 A | 8/2000 | Alt | |
| 6,110,204 A | 8/2000 | Lazarov et al. | |
| 6,174,329 B1 | 1/2001 | Callol et al. | |
| 6,261,322 B1 | 7/2001 | Despres, III et al. | |
| 6,293,966 B1 | 9/2001 | Frantzen | |
| 6,312,456 B1 | 11/2001 | Kranz et al. | |
| 6,334,871 B1 | 1/2002 | Dor et al. | |
| 6,355,058 B1 | 3/2002 | Pacetti et al. | |
| 6,361,557 B1 | 3/2002 | Gittings et al. | |
| 6,375,655 B1 | 4/2002 | Xdeblick et al. | |
| 6,379,383 B1 | 4/2002 | Palmaz et al. | |
| 6,387,121 B1 | 5/2002 | Alt | |
| 6,402,777 B1 | 6/2002 | Globerman et al. | |
| 6,447,664 B1 | 9/2002 | Taskovics et al. | |
| 6,464,723 B1 | 10/2002 | Callol | |
| 6,471,721 B1 | 10/2002 | Dang | |
| 6,497,671 B2 | 12/2002 | Ferrera et al. | |
| 6,497,803 B2 | 12/2002 | Glocker et al. | |
| 6,503,271 B2 | 1/2003 | Duerig et al. | |
| 6,537,310 B1 | 3/2003 | Palmaz et al. | |
| 6,540,774 B1 | 4/2003 | Cox | |
| 6,554,854 B1 | 4/2003 | Flanagan | |
| 6,585,757 B1 | 7/2003 | Callol | |
| 6,613,091 B1 | 9/2003 | Zdeblick et al. | |
| 6,616,765 B1 | 9/2003 | Castro et al. | |
| 6,620,192 B1 | 9/2003 | Jalisi | |
| 6,635,082 B1 | 10/2003 | Hossainy et al. | |
| 6,638,301 B1 | 10/2003 | Chandrasekaran et al. | |
| 6,641,607 B1 | 11/2003 | Hossainy et al. | |
| 6,645,206 B1 | 11/2003 | Zdeblick et al. | |
| 6,652,579 B1 | 11/2003 | Cox et al. | |
| 6,716,444 B1 | 4/2004 | Castro et al. | |
| 6,730,197 B2 * | 5/2004 | Wang et al. | 204/298.11 |
| 6,820,676 B2 | 11/2004 | Palmaz et al. | |
| 6,913,998 B2 * | 7/2005 | Jankowski et al. | 438/666 |
| 6,938,668 B2 | 9/2005 | Whicher et al. | |
| 7,079,903 B2 | 7/2006 | O'Brien | |
| 7,195,641 B2 | 3/2007 | Palmaz et al. | |
| 7,335,426 B2 | 2/2008 | Marton et al. | |
| 7,491,226 B2 | 2/2009 | Palmaz et al. | |
| 7,625,594 B2 | 12/2009 | Palmaz et al. | |
| 7,641,680 B2 | 1/2010 | Palmaz et al. | |
| 7,670,690 B2 | 3/2010 | Marton et al. | |
| 2001/0032005 A1 | 10/2001 | Gelb et al. | |
| 2001/0032013 A1 | 10/2001 | Marton et al. | |
| 2001/0036530 A1 | 11/2001 | Noda et al. | |
| 2002/0016635 A1 * | 2/2002 | Despres et al. | 623/23.5 |
| 2002/0049402 A1 | 4/2002 | Peacock et al. | |
| 2002/0144903 A1 | 10/2002 | Kim et al. | |
| 2002/0195336 A1 * | 12/2002 | Glocker et al. | 204/298.19 |
| 2003/0036792 A1 | 2/2003 | Richter et al. | |
| 2004/0068323 A1 | 4/2004 | Christensen et al. | |
| 2005/0165472 A1 | 7/2005 | Glocker et al. | |
| 2005/0187466 A1 | 8/2005 | Glocker et al. | |
| 2005/0266040 A1 | 12/2005 | Gerberding et al. | |
| 2005/0288773 A1 | 12/2005 | Glocker et al. | |
| 2006/0200231 A1 | 9/2006 | O'Brien et al. | |
| 2007/0106374 A1 | 5/2007 | Glocker et al. | |
| 2007/0250156 A1 * | 10/2007 | Palmaz | 623/1.39 |

FOREIGN PATENT DOCUMENTS

| | | |
|---|---|---|
| WO | WO 01/55473 | 8/2001 |
| WO | WO 01/87371 | 11/2001 |
| WO | WO 02/076525 | 10/2002 |

OTHER PUBLICATIONS

L.A. Cyster, D.M. Grant, K.G. Parker, T.L. Parker, The effect of surface chemistry and structure of titanium nitride (TiN) films on primary hippocampal cells, Biomolecular Engineering, vol. 19, Issues 2-6, Aug. 2002, pp. 171-175.*

Glocker, D., "Hollow-Cathode Sputter Deposition of SC Films", Superconductor Industry, Spring 1994, pp. 10-12.

John A. Thornton, High Rate Thick Film Growth, 1977, pp. 239-260, Annual Reviews, Inc.

Dean W. Matson, Edwin D. McClanahan, Sabrina L. Lee and Donald Windover, Properties of Thick Sputtered Ta Used for Protective Gun Tube Coating, Surface and Coatings Technology, 2001, pp. 344-350.

Nanobumps Enhance Implants, R&D Magazine, Jan. 2004, p. 46, US.

W. D. Westwood, Calculation of Deposition Rates in Diode Sputtering Systems, J. ac. Sci. Technol., pp. 1-9, Jan./Feb. 1978.

Precision Silver Coating, www.medicalsysforindustry.com/page65.htm.

Precision Gold Coating, www.medicalsysforindustry.com/teflonmetal.htm.

Precision Titanium Coating, www.medicalsysforindustry.com/page66.htm.

\* cited by examiner

POROUS COATINGS FOR BIOMEDICAL IMPLANTS

CROSS REFERENCE TO RELATED APPLICATION

This application claims the benefit of U.S. provisional application No. 60/583,416 filed Jun. 28, 2004, the entire disclosure of which is incorporated herein by reference in its entirety for any and all purposes.

TECHNICAL FIELD

The present invention relates to medical devices.

BACKGROUND

Orthopedic implants such as artificial knees and hips are critical to improving the quality of life for millions of people each year. As the population ages, the need for such implants will continue to increase. An important attribute of these devices is how well the body's bone and tissue can bond to them.

One method that is known in the art to promote the attachment of implants to bone is to apply hydroxyapatite to their surface using plasma spray technology. Hydroxyapatite is a natural material to which bones will attach. However, this method is expensive and hydroxyapatite is brittle and difficult to make adhere to the smooth surfaces of implants.

It is also known that open, porous structures can promote the attachment of natural tissue to implanted material. Tantalum is often chosen for such applications because it is extremely corrosion resistant and biocompatible. Porous tantalum can be used as an element in orthopedic devices or they can be made entirely of porous tantalum. This is the subject of U.S. Pat. Nos. 5,282,861; 5,669,909; 5,984,967; 6,645,206; 6,613,091 and 6,375,655. It is well known in the art that porous tantalum can be formed by sintering tantalum powder under the proper conditions. Other methods for producing porous tantalum, such as using chemical vapor deposition to fill a vitreous carbon matrix with tantalum, are also known.

Tantalum, however, is a relatively soft, ductile metal and an implant made entirely of porous tantalum would not be strong enough to be used for a highly stressed part in a hip or knee, for example. In applications requiring mechanical strength, alloys containing cobalt, chromium, nickel, titanium and other materials such as stainless steel are often used. In such cases, it is desirable to create a porous surface layer to help natural tissue to bond. Attaching a porous tantalum layer to such materials requires several steps. This is the subject of U.S. Pat. No. 6,063,442, which describes a method of clamping a porous material to a substrate and using chemical vapor deposition to bond the two. However, in addition to the cost of this method, processing temperatures as high as 925 C are required. These high temperatures can alter the mechanical properties of many alloys. Moreover, clamping a porous layer to the complicated shapes used in orthopedic devices is difficult.

Recently it has been found that small surface features with sizes of approximately 100 nanometers (nm) can promote the attachment of bone cells to metals (*Nanobumps Enhance Implants*, R&D Magazine, January 2004, p. 46). Surface features of tens to hundreds of nm in size mimic the texture of natural bone and are also comparable to the size of the proteins needed to promote tissue growth. It is believed that the precise shape of these features is not critical to their usefulness and they can be regular or irregular in shape.

Therefore, what is needed is a coating having surface roughness on the order of ten to hundreds of nanometers that can be applied directly to orthopedic implants in a simple manner.

SUMMARY

The present invention is directed towards a medical device having a microscopically rough outer coating that can be applied to orthopedic implants in a simple manner.

A medical device in accordance with the present invention can include an implant and a biomedically compatible, microscopically rough coating applied to the implant via physical vapor deposition.

The coating is configured to serve as a bonding layer between the implant and animal tissue. The coating preferably has surface features having a size between 10 nm and 1000 nm. These features may vary in size. The coating can comprise one of the group of tantalum, titanium nitride, titanium, molybdenum, chromium and zirconium. Preferably, the coating has a thickness between 0.1 and 10 micrometers. In the preferred embodiment, the coating has pores. A drug may reside within the pores.

The device can have a second coating. The second coating can be applied directly to the implant and the microscopically rough, preferably porous, coating can be applied to the second coating. Optionally, the second coating protects the implant from corrosion and is nonporous.

The physical vapor deposition comprises one of the group of sputtering, cathodic arc deposition or thermal evaporation. The coating preferably is applied to the implant via one of a generally oblique coating flux or a low energy coating flux.

A process for depositing a coating on a biomedical implant comprises the steps of:
 maintaining a background pressure of gas in a sputter coating system containing at least one sputter target;
 applying a voltage to the target to cause sputtering; and
 sputtering for a period of time to produce a microscopically rough coating on the implant.

BRIEF DESCRIPTION OF THE DRAWINGS

These and other features, aspects and advantages of the present invention will become better understood with regard to the following description, appended claims, and accompanying drawings where:

DESCRIPTION

Figure 1:
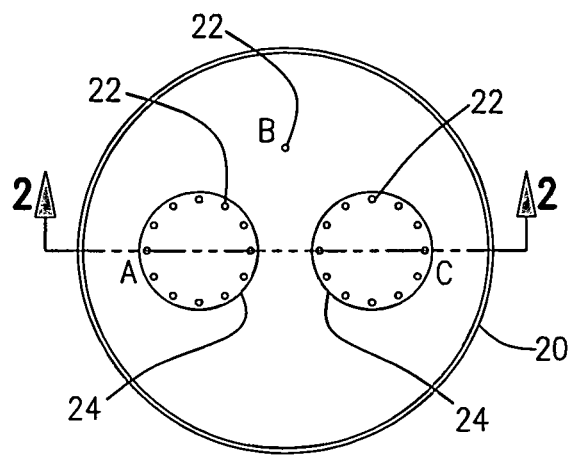
FIG. 1 is a top view of a target surrounding substrates.

The present invention is directed towards a medical device having a microscopically rough outer coating that adheres well to biomedical implants and improves the adhesion of natural tissue and bone. By microscopically rough, we mean having surface features, including but not limited to, pores, bumps, hollows or combinations thereof, on the order of 10's to 100's of nanometers in size. These features can be seen using a scanning electron microscope.

The coating preferably is applied by physical vapor deposition processes, such as sputtering, cathodic arc or thermal evaporation. In some cases the coatings can also be infused with materials intended for a variety of purposes, such as to prevent inflammation or promote tissue growth.

Tantalum is biomedically compatible and corrosion resistant, making it an attractive material for the microscopically rough coatings in this application, although other materials may be used, such as, but not limited to, titanium, titanium nitride, molybdenum, niobium, chromium and so on.

It is well known in the art of physical vapor deposition that low homologous coating temperatures (the ratio of the substrate temperature to the melting point of the coating material in degrees Kelvin) often result in microscopically rough, porous coatings. However, poor coating adhesion also often results from these coating conditions. Nevertheless, we have unexpectedly found that rough, porous coatings deposited under the correct conditions are able to adhere to the types of materials used in biomedical implants without unacceptable flaking.

A large number of experiments were done to examine the influence of the deposition conditions and system geometry on the structure of the resulting coatings. In all cases the implant materials, sometimes referred to as "substrates" herein, were cleaned with a warm aqueous cleaner in an ultrasonic bath. Crest 270 Cleaner (Crest Ultrasonics, Inc.) diluted to 0.5 pounds per gallon of water was used at a temperature of 55 C. This ultrasonic detergent cleaning was done for 10 minutes. The substrates were then rinsed for 2 minutes in ultrasonically agitated tap water and 2 minutes in ultrasonically agitated de-ionized water. They were then blown dry with nitrogen and further dried with hot air. The manner in which the substrates were cleaned was found to be very important. When the substrates were cleaned ultrasonically in acetone and isopropyl alcohol, a residue could be seen on the substrates that resulted in poor adhesion.

In addition to conventional cleaning, it is possible to use plasma cleaning as an integral part of the coating process. In that case, an initial high voltage can be applied to the substrates in order to sputter clean them and remove any residual contamination. The initial high voltage preferably is between approximately 100 and 600 volts and is preferably applied for about 20 minutes. This cleaning can be done with the deposition source off or it can be carried out during the initial stages of deposition. Times for such cleaning can be from less than a minute to several minutes. A second lower voltage can be applied, preferably for a period of time between about 1 and 5 hours.

Figure 2:
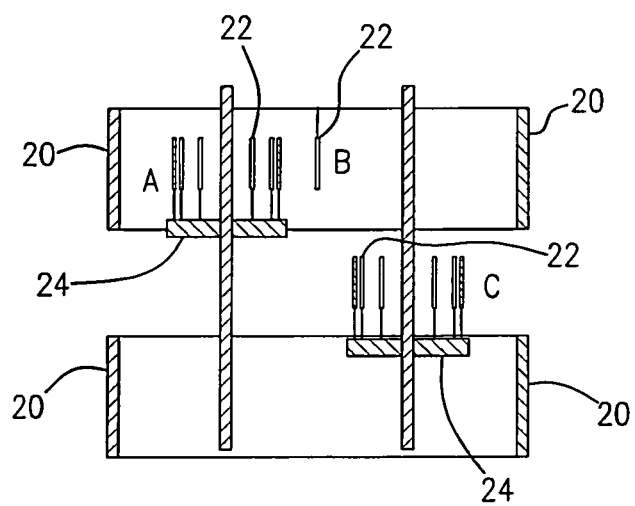
FIG. 2 is a side cross-sectional view of the target surrounding substrates of FIG. 1.

Two different unbalanced cylindrical magnetron sputtering systems, as described in U.S. Pat. No. 6,497,803, which is incorporated herein by reference, were used to deposit the coatings. FIGS. 1 and 2 illustrate the setup for System 1. System 1 had targets 20, each 34 cm in diameter and 10 cm high, separated by 10 cm. System 2 was similar to System 1 but only used the top target shown in FIGS. 1 and 2, which was 19 cm in diameter. Preferably Ar, Kr or Xe was used as the sputtering gas, sometimes in mixtures with other gases. In general, the targets can be cylinders or plates 24 or any other form known in the art. Other devices well known to those in the art, such as vacuum pumps, power supplies, gas flow meters, pressure measuring equipment and the like, are omitted from FIGS. 1 and 2 for clarity.

The targets 20 were driven with either DC power or AC power. Preferably, two independent power supplies are used in the case of DC power and a single power supply connected to both targets is used in the case of AC power, in a manner well known to those skilled in the art. The voltage can be applied continuously or in pulses or in any other manner known in the art. Preferably, the voltage produces a deposition rate of one to 5 microns per hour.

The sputtering targets 20 were preconditioned at the process power and pressure for approximately 10 minutes prior to starting the depositions. During this step a shutter isolated the substrates 22 from the targets 20. Importantly, this preconditioning process heated the shutter and caused the temperature of the substrates 22 to rise. This preheating allowed the substrates 22 to further degas and approach the actual temperature of the coating step. The substrates 22 were not directly heated or cooled in any way during deposition and their time-temperature history was determined entirely by the coating process. During sputtering the substrate temperature preferably remains between 150 and 450 degrees Celsius. This is a very low homologous temperature for materials such as Ta, Ti, TiN, Mo, Cr and Nb. After opening the shutter, the coating time was adjusted so that a coating thickness of approximately 10 microns resulted. At a power of 4 kW the time for Ta was 2 hours and 15 minutes and at a power of 2 kW the time was 4 hours and 30 minutes. For clarity, these are the time/power combinations that achieve a 10 micron coating thickness for Ta. In some of the examples below, the coating times vary from those given above. When this is the case, the coating thickness varies also.

Example 1

Electropolished nickel-titanium alloy substrates 22 were placed at three positions in System 1, as shown in FIGS. 1 and 2:

Position A—The substrates 22 were held on a 10 cm diameter plate 24 that rotated about a vertical axis, which axis was approximately 7 cm from the cathode centerline. The vertical position of the substrates 22 was in the center of the upper cathode. Finally, each substrate was periodically rotated about its own axis by a small "kicker" in a manner well known in the art.

Position B—The substrates 22 were suspended from a rotating axis that was approximately 7 cm from the chamber centerline. The vertical position of the substrates 22 was in the center of the upper cathode.

Position C—The substrates 22 were on a 10 cm diameter plate 24 that rotated about a vertical axis, which axis was approximately 7 cm from the cathode centerline, as in position A. However, the vertical location of the substrates 22 in position C was in the center of the chamber midway between the upper and lower cathodes. Finally, each substrate was periodically rotated about its own axis with a "kicker."

The targets 20 were comprised of Ta and were each driven at a DC power of 2 kW. A bias of −150V was applied to the substrates 22 during the coating. The sputtering pressure was 3.4 mTorr and the sputtering gas was Kr. The coating time was 2 hours and 15 minutes, resulting in a coating thickness of about 10 microns.

There was a marked difference in the appearance of the substrates 22 at the three positions. Those in positions A and B were shiny and metallic, while the substrate in position C had a dull, matte metallic appearance.

Example 2

To further explore the influence of the substrate position in the chamber on the appearance of the coating, an experiment was done in which only the top Ta target was operating at a power of 2 kW in System 1. The sputtering pressure was 3.4 mTorr, the sputtering gas was Kr and the coating time was 3 hours and 20 minutes. Nickel titanium alloy substrates 22 were located in positions B and C shown in FIGS. 1 and 2.

The substrate in position B was shiny and metallic looking. The substrate in position C was somewhat shiny on the top, but was black at the bottom. It is well known that a black appearance can result from a surface with microscopic features on the order of hundreds of nanometers because of the scattering and absorption of visible light.

The adhesion of the coatings was tested using 3M Scotch Brand tape. The tape was pressed into the substrates 22 and pulled away. There was significant removal of the coating from the substrate in position B, but only one small spot of removal at the top of the substrate in position C and no removal from the lower portion with the black appearance.

In this experiment the substrate in position C received a generally more oblique and lower energy coating flux than the substrate in position B. By an oblique coating flux we mean that the majority of the depositing atoms arrive in directions that are not generally perpendicular to the surface being coated. Some of the atoms arriving at the surfaces of the substrate in position C from the upper target will have done so without losing significant energy or directionality because of collisions with the background sputter gas. Those atoms, most of which will come from portions of the target close to the substrate as seen in FIG. 2, will create an oblique coating flux. Other atoms will undergo several collisions with the background gas and lose energy and directionality before arriving at the substrate surfaces. Those atoms, which will generally come from portions of the target at greater distances, will form a low average energy coating flux.

Westwood has calculated ("Calculation of deposition rates in diode sputtering systems," W. D. Westwood, Journal of Vacuum Science and Technology, Vol. 15 page 1 (1978)) that the average distance a Ta atom goes in Ar at 3.4 mTorr before its energy is reduced to that of the background gas is between about 15 and 30 cm. (The distance would be somewhat less in Kr and the exact value depends on the initial energy of the Ta atom.) Because our cylindrical targets 20 have an inside diameter of approximately 34 cm, substrates 22 placed in the planes of the targets (positions A and B) receive a greater number of high energy, normal incidence atoms and those placed between the targets 20 (position C) receive a greater number of low energy and/or oblique incidence atoms.

The geometry of the cylindrical magnetron arrangement shown in FIGS. 1 and 2 assures that atoms arriving at the surface of substrates 22 placed in position C will do so either at relatively oblique angles or with relatively low energy. Referring to FIG. 2, when the substrates 22 are close to the targets 20 where the arriving Ta atoms have lost little energy, the atoms arrive at oblique angles. And when the substrates 22 move closer to the center of the chamber where the arrival angles are less oblique, they are farther from the target surface so that the arriving Ta atoms have lost more energy through gas collisions.

Typically, sputtered atoms leave the target surface with average kinetic energies of several electron volts (eV). As described by Westwood, after several collisions with the background gas the sputtered atoms lose most of their kinetic energy. By low energy, we are referring to sputtered atoms that have average energies of approximately 1 eV or less. Westwood's calculations can be used to estimate the target to substrate spacing required to achieve this low average energy for a given sputtering pressure. Furthermore, it is well known to those skilled in the art that atoms deposited by evaporation have average energies below approximately one eV when they leave the evaporation source. Therefore, scattering from the gas in the chamber is not required to produce a low energy coating flux in the case of evaporated coatings.

It is widely known in the art that when the atoms in a PVD process arrive with low energies or at oblique angles to the substrate surface, the result is a coating that can have a rougher surface and lower density than a coating made up of atoms arriving at generally normal incidence or with higher energies. As discussed earlier, the black appearance of the coating in position C may be the result of coating roughness on the order of tens to hundreds of nanometers in size. Those skilled in the art will recognize that the rough, porous coatings we are describing are those sometimes called Zone 1 coatings for sputtered and evaporated materials (see, for example, "*High Rate Thick Film Growth*" by John Thornton, Ann. Rev. Mater. Sci., 1977, 239-260). Deposition conditions that produce such coatings typically lead to poor adhesion. Surprisingly, we have found excellent adhesion in such coatings made by our methods.

Example 3

Figure 3:
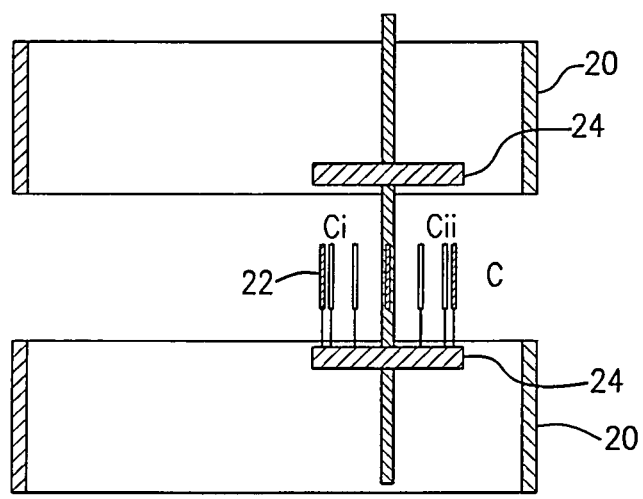
FIG. 3 is a side cross-sectional view of the target surrounding substrates in position C of FIG. 1 with a plate above the substrates.

Further evidence of the importance of the coating geometry and sputtering conditions is seen in the following experiment, illustrated in FIGS. 2 and 3. A number of Ta coatings were done on nickel titanium alloy substrates 22 in System 1 using Kr at a pressure of 3.4 mTorr, a DC power of 1 kW on each target and a bias of −50 V and the plate 24 shown in FIG. 2 position C. As before, the substrates 22 were rotating about the vertical rod as well as about their own axes. In order to increase the effect of position in this experiment, 10 cm long substrates 22 were used. The coatings made this way were matte black at the bottom but had a slightly shinier appearance at the top. In contrast, when coatings were done on substrates 22 under identical conditions, except that a second plate 24 was placed above the substrates as shown in FIG. 3, the substrates were a uniform black from bottom to top.

The non-uniformity in appearance that resulted with the fixturing shown in FIG. 2 is further evidence that the coating structure depends on the details of how the substrates 22 and sputter targets 20 are positioned relative to one another. As discussed earlier, when the substrates 22 are in position Ci in FIG. 3, they receive very oblique incidence material from portions of the targets 20 that are close, while the coating material that arrives from other portions of the targets has to travel farther. Therefore, all of the coating flux has arrived at oblique incidence or has traveled a considerable distance and has lost energy and directionality through collisions with the sputtering gas. When the substrates 22 are in position Cii in FIG. 3, however, they receive a somewhat less oblique coating from all directions. In the configuration shown in FIG. 2, however, the bottoms of the substrates 22 are shielded from the more direct flux from the bottom target by the plate 24 that holds them, but the tops of the substrates 22 are not similarly shielded from the more direct flux coming from the top target. By adding the plate 24 above the substrates 22 as well, as shown in FIG. 3, the more direct coating flux is shielded at all points on the substrates and the coating material either arrives at relatively oblique incidence or after scattering from the background gas and losing energy and directionality. The plate 24 above the substrates 22 restores symmetry and the coatings on the substrates become uniformly black.

Example 4

Figure 4:
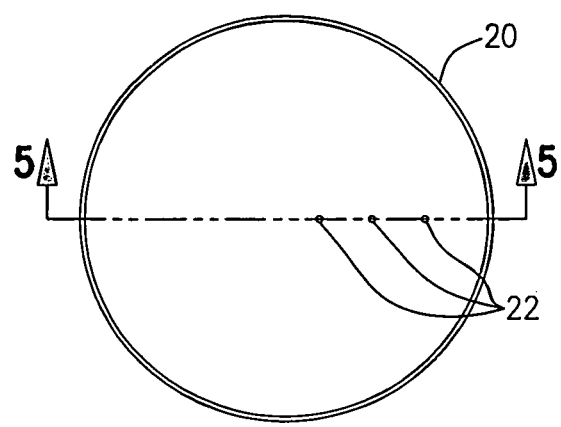
FIG. 4 is a top view of a target surrounding substrates in another configuration.
Figure 5:
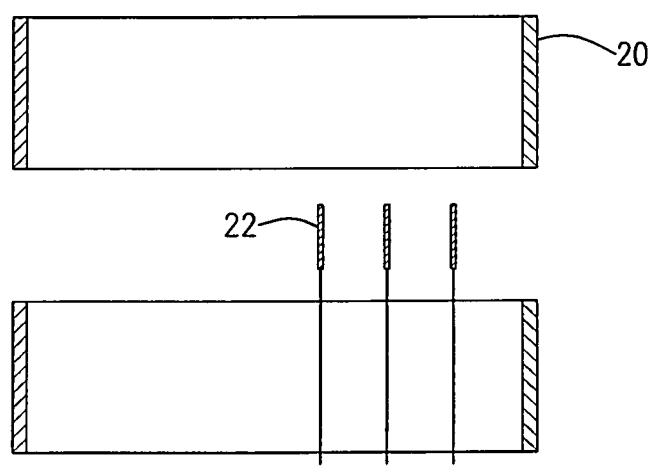
FIG. 5 is a side cross-sectional view of the target surrounding substrates of FIG. 4.

Other methods of positioning and moving the substrates 22 within the chamber can also produce results similar to those described above and are within the scope of the invention. In another experiment three nickel titanium alloy substrates 22 were located in System 1 as shown in FIGS. 4 and 5. FIG. 4 is a top view of the substrate locations and FIG. 5 is a cross-sectional view of the same arrangement. All three were held fixed at their positions within the chamber and were rotated about their individual axes during the coating run. The innermost substrate was 3 cm from the cathode centerline, the middle substrate was 7 cm from the cathode centerline and the outermost substrate was 11 cm from the cathode centerline. The Ta deposition was done at a DC power of 1 kW on each target, a Kr pressure of 3.4 mTorr and with the substrates 22 biased at −50 V. All three substrates 22 had a matte black appearance and none of the coating could be removed from any of the substrates using the tape test. Therefore, substrates 22 placed at virtually any radial position within the cathodes and rotating about their individual axes will receive a satisfactory coating, provided they are located between the targets in the axial direction.

An alternative to oblique incidence coatings or large target to substrate distances in order to reduce the energy of the arriving atoms through collisions is to raise the pressure of the sputtering gas. It is widely known in the art that high sputtering pressures lead to less dense coatings with microscopically rough surfaces. However, we have found that this approach can produce less desirable results.

Sputtering takes place under conditions of continuous gas flow. That is, the sputtering gas is brought into the chamber at a constant rate and is removed from the chamber at the same rate, resulting in a fixed pressure and continuous purging of the gas in the chamber. This flow is needed to remove unwanted gases, such as water vapor, that evolve from the system during coating. These unwanted gases can become incorporated in the growing coating and affect its properties.

The high vacuum pumps used in sputtering, such as diffusion pumps, turbomolecular pumps and cryogenic pumps, are limited with respect to the pressure that they can tolerate at their openings. Therefore, it is well known that in order to achieve high sputtering pressures it is necessary to "throttle" such pumps, or place a restriction in the pump opening that permits the chamber pressure to be significantly higher than the pressure at the pump. Such "throttling" necessarily reduces the flow of gas through the chamber, or gas throughput. Surprisingly, we have found that adherent coatings depend on having high gas throughputs and pumping speeds, which is only practical at relatively low sputtering pressures. Our results indicate that during sputtering, preferably the gas throughput is between approximately 1 and 10 Torr-liters per second.

Example 5

In one experiment, a single target of System 2 having an inside diameter of 19 cm and length of 10 cm was used to coat an electropolished nickel-titanium alloy substrate with Ta at a sputtering pressure of 30 mTorr in Ar. In order to achieve this pressure, it was necessary to throttle the turbomolecular high vacuum pump on the vacuum system. The Ar flow during this coating was 0.63 Torr-liters per second, corresponding to a throttled pumping speed of 21 liters per second. The substrate was placed in the center of the target, approximately 9 cm from the target surface. The DC sputtering power to the target was 200 W. According to Westwood's calculations, the average distance a Ta atom travels in Ar at 30 mTorr before reaching thermal velocities is between 1.7 and 3.4 cm, depending on its initial energy. Therefore, these coating conditions should result in a very low-density and microscopically rough coating. The black appearance of the coated substrate confirmed that this was the case. However, the coating had very poor adhesion.

Example 6

In another experiment, Ta coatings were done on nickel titanium alloy substrates 22 in the C position using System 1 as shown in FIG. 2. The sputtering gas was Kr at a pressure of 3.4 mTorr. A DC power of 1 kW on each target was used together with a substrate bias of −50 V. The Kr flow was 28 standard cubic centimeters per minute, or 0.36 Torr-liters per second. At a pressure of 3.4 mTorr this corresponds to a throttled pumping speed of 104 liters per second during the process. The resulting black coatings had adhesion failure in several locations when using the adhesive tape test.

The position of the pump throttle was then changed and the Kr flow was increased to 200 standard cubic centimeters per minute or 2.53 Torr-liters per second. Coatings were done on substrates 22 in the C position at the same power, pressure and bias levels as before. The only difference was that the throttled pumping speed during this process was 744 liters per second. In this case there was no removal of the coating from the substrate using the tape test.

Based on the foregoing results, we conclude that adequate adhesion may not result at low gas throughputs, which are usually necessary to achieve high sputtering pressures. The sputtering pressure and system geometry must be chosen together so that the coating flux arrives at the substrate surface either at high angles of incidence or after the sputtered atoms have traveled a sufficient distance from the target to reduce their energies significantly.

Example 7

In order to test the usefulness of these coatings on other materials and examine their structure, electropolished stainless steel substrates 22 were located in position C in System 1 as shown in FIG. 2. The system was operated at a sputtering power of 1 kW on each Ta target, a bias of −50V applied to the substrates 22 and a pressure of 3.4 mTorr at a throughput of 2.5 Torr-liters per second. The deposition time was 2 hours and 15 minutes.

The coatings were black. The adhesion of the coatings to the substrates 22 was assessed using the tape test and several attempts failed to remove the coating. Moreover, the tape stuck much more tenaciously to the coated substrates 22 than to similar uncoated substrates. This indicates the presence of a rough, porous structure on the surface.

Figure 6:
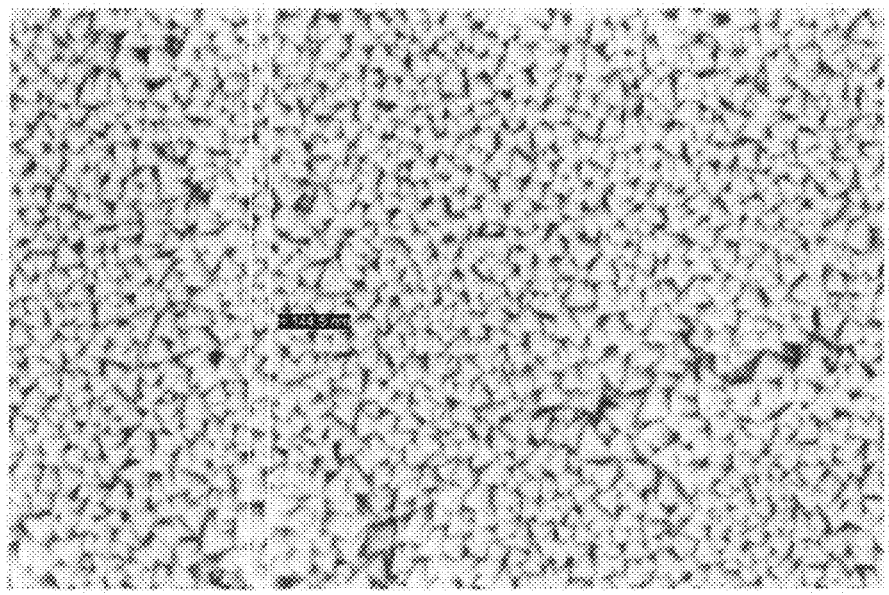
FIG. 6 shows a scanning electron micrograph of the surface of a Ta coating applied to a polished stainless steel surface.

FIG. 6 shows a scanning electron micrograph of the Ta coating on the stainless steel substrates 22. The substrates 22 were extremely smooth and the surface roughness and open structure that result from the coating are clearly visible. Many of the surface features have sizes of less than a micron, the very sizes that have been found effective for bone and tissue attachment. X-ray diffraction scans of this coating showed that it consisted almost entirely of the body centered cubic phase of Ta.

Example 8

In order to study the possibility of using materials other than Ta for porous coatings, System 1 was used to deposit TiN on polished stainless steel, which was located in position C shown in FIG. 2. Two Ti targets 20 were operated at a DC power of 3 kW each. The targets 20 were preconditioned in Ar with the shutter closed for 10.5 minutes. The shutter was then opened and Ti was deposited in Ar only at a pressure of 14 mT and gas flow of 1.4 Torr-liters per second. Nitrogen was then introduced at a flow rate of 0.6 Torr-liters per second and the pressure rose to 18 mT. The substrate had a −45 V DC bias applied during the coating, which lasted for a time of 1.5 hours.

Figure 7:
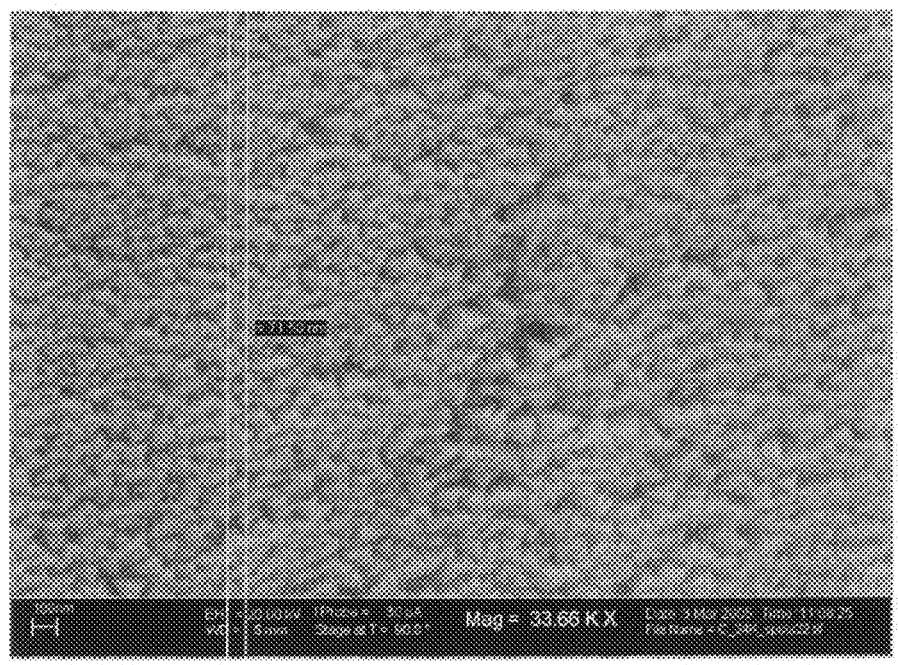
FIG. 7 shows a scanning electron micrograph of a TiN coating made according to the present invention.

FIG. 7 shows a scanning electron micrograph of the surface of the TiN coating that resulted. It also had a black appearance and the adhesion was excellent. The similarity between this and the Ta coating is obvious, and demonstrates that a large number of materials are candidates for producing microscopically rough, porous surfaces.

Figure 8:
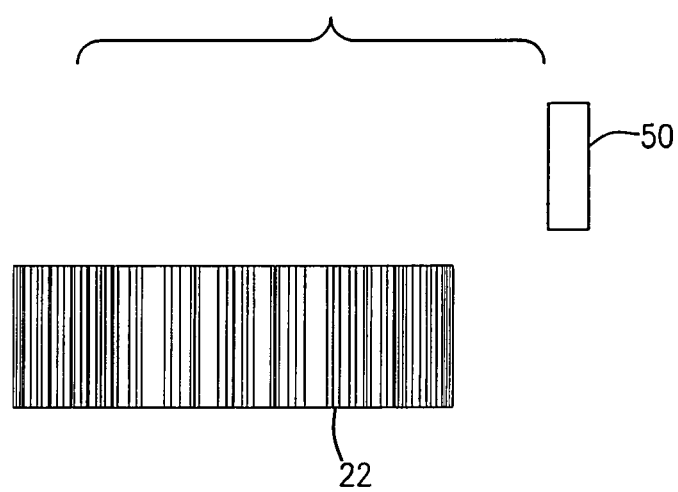
FIG. 8 is a side elevation view of substrates positioned beside a planar target at a high angle of incidence.

While the geometry of a cylindrical magnetron makes oblique incidence coatings possible in an efficient way, as we have shown, the same results can be accomplished using planar targets as well. In the case of planar targets, the requirement is to place the substrates 22 far enough from the target surface(s) that a large target-to-substrate distance is achieved. Alternatively, the substrates 22 could be placed to the side of a planar target 50 so that the material arrives at high incidence angles. This configuration is illustrated in FIG. 8. Of course, the substrate positions shown in the case of planar targets make inefficient use of the coating material and greatly reduce the deposition rate, which are undesirable from a manufacturing standpoint. Nevertheless, FIG. 8 illustrates how the inventive method could be used with geometries other than cylindrical magnetrons.

Example 9

We have also discovered that the initial coating conditions can influence the microstructure and crystalline phase of our coatings while preserving excellent adhesion. In one experiment, substrates 22 were loaded in Position C in System 1 using the setup shown in FIG. 2 with 34 cm diameter targets 20. With the shutter closed, the two Ta targets 20 were operated at 2 kW (1 kW each) at a Kr pressure of 3.6 mT and a Kr flow of 2.53 Torr-liters per second. After five minutes, and with the shutter still closed, a voltage of −200 V was applied to the substrates 22 in order to plasma clean them. The shutter was opened after five additional minutes and the coating was begun with a −200 V bias still applied to the substrates 22. These conditions were maintained for two minutes, at which time the voltage on the substrates 22 was reduced to −50 V and the coating was deposited under these conditions for 180 minutes. There was no flaking evident on these substrates 22.

Figure 9:
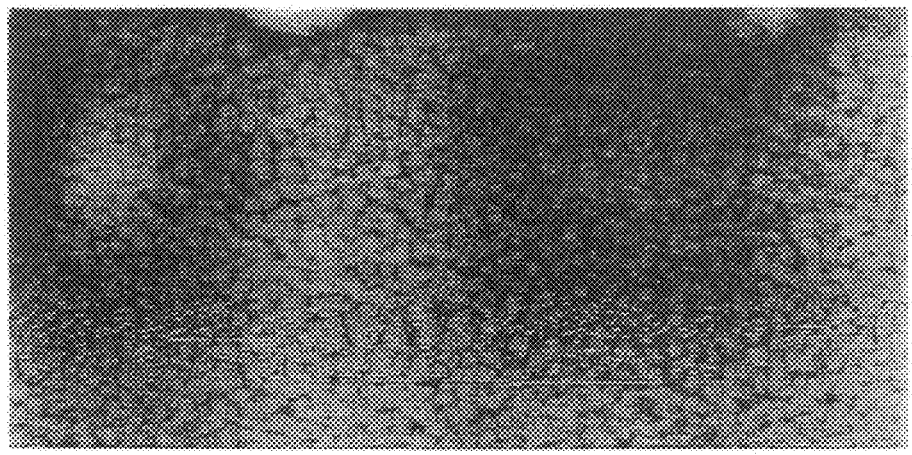
FIG. 9 shows an atomic force microscopy image of a Ta coating made according to another preferred embodiment of the present invention and applied to a polished nickel titanium alloy substrate.

Except for the initial five minutes of plasma cleaning and two minutes of −200 V bias sputtering, the conditions in the example above were the same as those used in Example 7 that produced the structure shown in FIG. 6 and the bcc crystalline phase. FIG. 9 is an atomic force microscope image of the resulting coating showing that the microstructure is changed by the initial conditions. While the features in FIGS. 6 and 9 are similar and both are microscopically rough, porous coatings, a close analysis shows that the structures in FIG. 6 are approximately 100 to 200 nm in size, while those in FIG. 9 are about twice as large. Moreover, the X-ray diffraction pattern shows that the crystalline phase of this coating shown in FIG. 9 was primarily tetragonal, with some bcc present.

Examples 7, 8, and 9 show that both a variety of materials and a variety of coating conditions can be used to make the microscopically rough, porous structures we are describing.

The combination of a very porous coating and excellent adhesion is very surprising. Oblique coating fluxes, thermalized coating atoms and low homologous temperatures are known to produce open, columnar coating structures and microscopically rough surfaces. However, such coatings typically have very poor adhesion. We have found conditions that produce such structures along with excellent adhesion.

An open, porous structure may have other advantages for implantable medical devices as well. For example, the microvoids in the coating would permit the incorporation of drugs or other materials that could diffuse out over time. Examples are superoxide dismutase to prevent inflammation, proteins to promote bone and tissue growth, or other materials that aid in the healing or growth process. In the art, drug-eluting coatings on substrates are presently made using polymeric materials. A porous inorganic coating would allow drug-eluting substrates to be made without polymeric overcoats.

The process described in the present invention provides a simple, inexpensive method for producing surfaces on implantable devices that aid in their attachment to bone and tissue. In addition to tantalum and titanium nitride, other coating materials that could be used include titanium, molybdenum, zirconium, chromium and other biocompatible elements. Moreover, it is possible to alter the surface layers of such coatings by anodizing or nitriding them or to deposit the oxides or nitrides of metals directly.

It is also possible to vary the conditions to produce a coating whose properties change throughout the thickness. For example, the first part of the coating could be applied under conditions that produce a fully dense coating. Then the conditions could be changed to those that produce a porous open structure. Such a coating could provide corrosion protection for the implant by virtue of the initial dense layer and good adhesion to bone through the microscopically rough layer above. In addition, drugs that diffuse over time can reside in the pores. Similarly, a nonporous coating can be applied to protect the substrate from corrosion. Then, an outer porous layer can be applied that easily bonds with animal tissue.

Although the present invention has been described in considerable detail with reference to certain preferred versions thereof, other versions are possible. For example, a substrate can be coated with a layer of a first material and a layer of a second, porous material. In another example, the microscopically rough features can be bumps instead of pores. The features also may be a combination of bumps and pores. Therefore, the spirit and scope of the appended claims should not be limited to the description of the preferred versions contained herein.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. §112.

We claim:

1. A process for depositing a coating on a biomedical implant comprising the steps of:
    placing the biomedical implant in a sputter coating system containing at least two cylindrical sputter targets each comprising a volume defined by respective outer circular planes and an inner surface of the target and a sputtering material disposed on the inner surface, the at least two cylindrical sputter targets spaced apart so that each respective volume does not overlap, the biomedical implant being positioned between and outside of the volumes of the at least two cylindrical sputter targets, wherein the biomedical implant is positioned greater than or equal to 5 cm and less than or equal to 15 cm from the at least two cylindrical sputter targets;
    maintaining a background pressure of gas in the sputter coating system, wherein the background pressure of gas ranges from 3.4 mTorr to 18 mTorr;
    applying a voltage to the at least two cylindrical sputter targets to cause sputtering; and
    sputtering for a period of time to produce a continuous coating on the implant, said continuous coating is a Zone 1 coating and comprises columnar structures and pores, wherein said pores occur within said continuous coating itself.

2. The process of claim 1 wherein the pores have a diameter between 10 nm and 1000 nm.

3. The process of claim 1 wherein the pores vary in diameter.

4. The process of claim 1 wherein the coating comprises tantalum, titanium nitride, titanium, molybdenum, chromium or zirconium.

5. The process of claim 1 wherein the coating is configured to serve as a bonding layer between the implant and bone.

6. The process of claim 1 wherein the coating is applied to the implant via one of a generally oblique coating flux or a low energy coating flux.

7. The process of claim 1 further comprising a second coating applied to the implant.

8. The process of claim 7 wherein the second coating is applied directly to the implant.

9. The process of claim 8 wherein the second coating protects the implant from corrosion.

10. The process of claim 8 wherein the second coating in nonporous.

11. The process of claim 1 wherein the coating has a thickness between 0.1 and 10 micrometers.

12. The process of claim 1 wherein the coating comprises at least one porous portion and at least one nonporous portion.

13. The process of claim 12 wherein the porous portion coats the nonporous portion.

14. The process of claim 1 further comprising a drug within the pores.

15. The process of claim 1 wherein said step of sputtering comprises sputtering a plurality of atoms and at least a portion of said plurality of atoms undergo collisions with said background pressure of gas whereby said at least a portion of said plurality of atoms lose energy and directionality.

16. The process of claim 1 wherein the continuous coating is formed on at least a portion of the implant to improve biomedical compatibility.

17. The process of claim 1 wherein the continuous coating comprises a metal.

18. The process of claim 1 wherein the biomedical implant is positioned midway between the volumes of the at least two cylindrical sputter targets.

19. A process for depositing a coating on a biomedical implant comprising the steps of: placing the biomedical implant in a sputter coating system containing at least two cylindrical sputter targets each comprising a volume defined by respective outer circular planes and an inner surface of the target and a sputtering material disposed on the inner surface, the at least two cylindrical sputter targets spaced apart so that each respective volume does not overlap, the biomedical implant being positioned between and outside of the volumes of the at least two cylindrical sputter targets, wherein the biomedical implant is positioned greater than or equal to 5 cm and less than or equal to 15 cm from the at least two cylindrical sputter targets; maintaining a background pressure of gas in the sputter coating system, wherein the background pressure of gas ranges from 3.4 mTorr to 18 mTorr; applying a voltage to the at least two cylindrical sputter targets to cause sputtering; and sputtering for a period of time to produce a continuous coating on the implant, said continuous coating is a Zone 1 coating and comprises columnar structures and pores wherein said pores occur within said continuous coating itself and wherein the coating is applied to the implant via one of a generally oblique coating flux or a low energy coating flux.

20. The process of claim 19 wherein the continuous coating is formed on at least a portion of the implant to improve biomedical compatibility.

21. The process of claim 19 further comprising a drug within the pores.

22. The process of claim 19 wherein the continuous coating comprises a metal.

23. The process of claim 19 wherein the biomedical implant is positioned midway between the volumes of the at least two cylindrical sputter targets.

* * * * *